United States Patent [19]

Fitzgerald et al.

[11] Patent Number: 5,157,962

[45] Date of Patent: *Oct. 27, 1992

[54] VIBRATORY VISCOMETER TRANSDUCER WITH ISOLATION SUPPORT FOR INLINE VISCOSITY SENSOR

[75] Inventors: John V. Fitzgerald, Metuchen; Teresa M. Walsh, Lawrenceville, both of N.J.

[73] Assignee: National Metal and Refining Company, Inc., Edison, N.J.

[ * ] Notice: The portion of the term of this patent subsequent to Nov. 26, 2008 has been disclaimed.

[21] Appl. No.: 738,922

[22] Filed: Aug. 1, 1991

Related U.S. Application Data

[60] Division of Ser. No. 667,238, Mar. 8, 1991, Pat. No. 5,067,344, which is a continuation of Ser. No. 348,695, May 8, 1989, abandoned.

[51] Int. Cl.$^5$ ............................................. G01N 11/16
[52] U.S. Cl. ................... 73/54.24; 73/54.37; 73/32 A
[58] Field of Search ............................. 73/32 A, 54, 59

[56] References Cited

U.S. PATENT DOCUMENTS

| | | | |
|---|---|---|---|
| 3,525,252 | 8/1970 | Kocatas | 73/54 |
| 4,023,400 | 5/1977 | November | 73/54 |
| 4,488,427 | 12/1984 | Matusik et al. | 73/59 |
| 4,558,588 | 12/1985 | Beaudoin et al. | 73/54 |
| 4,679,427 | 7/1987 | Kanda et al. | 73/54 |
| 4,685,066 | 8/1987 | Hafele et al. | 73/54 |
| 4,757,708 | 7/1988 | Hietaranta | 73/59 |
| 5,067,344 | 11/1991 | Fitzgerald et al. | 73/54 |

Primary Examiner—Hezron E. Williams
Assistant Examiner—Craig Miller
Attorney, Agent, or Firm—Arthur L. Lessler

[57] ABSTRACT

A viscosity measuring transducer especially useful for process control of fluids. The transducer oscillates an immersed blade sensor in the direction of the plane of the blade in order to maximize generation of shear waves and to minimize generation of compression waves. The transducer includes a bar which penetrates and is secured and peripheral sealed to an isolation plate which serves to protect the oscillation driver and pickup adjacent one end of the bar from the sensor blade to be immersed in a fluid adjacent the other end of the bar. Either the bar is relatively rigid and the isolation plate is relatively compliant, or vice versa. In the former case the isolation plate acts as an intrinsic flexible member of the oscillating system of the transducer; and in both cases the isolation plate constitutes a strong impermeable seal between the fluid and the driver/pickup mechanism. The isolation plate may be corrugated or ribbed to allow vibratory motion in the desired direction (parallel to the sensor blade major surfaces) while resisting movement in the direction perpendicular thereto.

7 Claims, 4 Drawing Sheets

VIBRATORY VISCOMETER TRANSDUCER WITH ISOLATION SUPPORT FOR INLINE VISCOSITY SENSOR

This is a division of application Ser. No. 07/667,238, filed Mar. 8, 1991, now U.S. Pat. No. 5,067,344, which is a continuation of Ser. No. 07/348,695, filed May 8, 1989, now abandoned.

BACKGROUND OF THE INVENTION

This invention relates to an improved transducer for use in a vibratory viscometer; which transducer is particularly useful for, but not limited to, the inline detection under flow conditions of viscous and elastic properties of fluids being processed.

Vibratory viscometers are well known in the art and generally employ a transducer which has an immersible portion which is vibrated with a small amplitude. Fluid viscosity/density/viscoelasticity can be determined from the frequency and/or amplitude changes in the vibration and/or the power required to sustain the vibration when the immersible portion of the transducer is immersed in a fluid.

Such transducers generally comprise (i) an immersible tip, (ii) an electromagnetic drive and (iii) an electromagnetic or piezoelectric pickup. Transducers of this type are described by J. G. Woodward in "Vibrating Plate Viscometers", Electronics, February 1952; and by J. D. Ferry in "Viscoelastic Properties of Polymers", published by John Wiley & Sons, New York, 1970.

Prior Oscillatory Viscometers

The oscillatory viscometers described below exemplify the prior art, and have transducers which interact with the fluid being measured by "surface loading" of an oscillating portion of the transducer; said term having been used J. D. Ferry in his aforementioned publication.

The oscillating surface generates shear waves in the liquid or other fluid. Viscoelasticity is measured in terms of the characteristic impedance of the liquid.

In the vibrating plate viscometer described in the aforementioned publication of J. G. Woodward, the moving end of a vibrating reed supports a plate which detects viscous resistance of the fluid in which it is immersed. The reed is driven electromagnetically and the oscillations are picked up by a barium titanate piezoelectric block. The reed is clamped at one end, exposing the driver and pickup to fluid vapors. The viscometer measurements are confined to viscous loss determined from the decrease in amplitude of oscillation observed when the plate is immersed. The plate vibrates in a direction essentially perpendicular to its major surfaces.

A. Konno, S. Malsino and M. Kameko, in Japan Journal of Applied Physics 189 (1968), reported their measurements of storage modulus and viscous loss by oscillating an immersed very thin microscope slide at 100 Hz. This apparatus, driven by a moving coil, is reported as strictly a research instrument. The internal workings of the transducer were exposed to fluid vapors.

A viscometer known as Le Viscosimetre "Pivert" is sold by the Societe Francis de Service, 8 rue Nobel Zl, 45700 Villemander, France. The sensor tip of this viscometer (also called "Sofraser") is a U-shaped stainless steel needle. One leg of the U-shaped needle is mechanically driven sinusoidally at 125 Hz., which is near the mechanical resonance frequency of the transducer. Both legs of the needle are clamped at nodal points. Frequencies are measured at both legs. The phase difference between the frequencies is transformed into a voltage or current related to the viscosity of the liquid in contact with the needle. The manufacturer states that installation conditions can decrease accuracy and therefore should be carefully checked to be sure of optimum accuracy. The range of viscosity measurement is 0.5 to 15,000 mPa.s (cPs). The environmental limits of utilization are 200° C. and pressure to 100 bars.

The Dynatrol Viscosity Detector is sold by Automation Products, Inc., 3030 Max Roy, Houston, Tex. 77008. Although this instrument does not employ a blade sensor, it does employ welding at the node point of a resonating system in order to isolate the oscillating probe from the driver and pickup. Viscosity-density product is detected by an immersed 5 inch long stainless steel probe. The probe is made from a stainless steel rod and bent very much like a hairpin. Both ends of the rod are welded at nodal points to a supporting plug. One end of the probe penetrates into the housing where it is electromagnetically driven to resonate in flexure at 120 Hz. The other end of the probe also penetrates through the plug into the housing where there is an electromagnetic pickup coil. The decrease in amplitude of vibration of the immersed probe due to interaction with the fluid is electronically converted to viscosity-density product.

The Labor-Viskosimeter QV35 is marketed by Bopp & Reuther GmbH, Car-Reuther-Strasse 1, Postfach 310140, D-6800 Mannheim 31, West Germany. This instrument uses an oscillating transducer to measure viscosities of laboratory samples of liquids by means of a quartz crystal sensor oscillating in torsion at 55 KHz. The damping effect of the fluid being measured on the amplitude of oscillation is converted into viscosity. The temperature range of this instrument is limited to −50° to 150° C.

The Model 1800 Viscometer sold by Combustion Engineering, Inc., P.O. Box 831, Lewisburg, W.Va. 24901 utilizes an oscillating sensor blade. Short pulses of current are applied to the top of the blade, which is composed of a magnetostrictive alloy. The blade protrudes through a metal diaphragm. Each pulse causes the blade to vibrate at its natural frequency of 28 KHz. When the amplitude of vibration of the immersed blade has fallen to a preset value that relates to the viscosity of the liquid, another pulse is automatically applied. The change in pulse rate is proportional to the square root of viscosity-density product. The range of viscosities measured is from 0 to 5,000 centipoise x grams/cm.$^2$ in ranges of 0–50, 0–500, and 0–5000. This viscometer was produced for many years by Bendix Corporation, and was first described as the Ultra-Viscoson by W. Roth and S. R. Rich in Jr. Applied Phy. 24 940–950, July 1953. The Bendix Ultra-Viscoson is described on page 308 of Viscosity and Flow Measurement by S. R. Van-Waser, S. W. Lyons, K. Y. Kim and R. E. Cowell, Interscience Publishers, New York, 1963. Shortcomings included very high frequency of measurement, fragility of very thin strip (blade), lack of sensitivity at very low viscosities, need to flick the strap from time to time to relieve strains in the magnetostrictive alloy; and since strips were easily bent, replacement blades needed to be available.

Hermetic sealing between driver and pickup is a feature of the "Vibrating Sphere" and "Viscoliner" oscillating viscometers of Nametre Company, 101 Forrest St., Metuchen, N.J. 08840, the assignee of the present application. However, the spherical and cylindrical sensors are somewhat obstructive to flowing fluids, particularly slurries. In order to reduce the obstruction to flow, the diameter of the pipe in which the fluid flows needs to be increased so as to satisfactorily accept the oscillating sensor. Since the mode of oscillation has two degrees of freedom, care must be taken to chose between in-phase and out-of-phase torsional motion. Further, the oscillating surface generates diverging shear waves that may be so long in wavelength that they are not conveniently reflected for accurate measurement of highly viscoelastic fluids.

U.S. Pat. No. 4,729,237 describes a tuning fork transducer, each of the two arms of the fork having welded to it a blade that is oscillated in the liquid. It is claimed that one blade on one arm of the tuning fork gave less accurate viscosity measurements than having blades on each arm. This viscometer is a laboratory instrument. The specification describes vertical motion of a sample container to immerse the two blades in the liquid.

Objects of the Present Invention

For a long time there has been great need for small inline blade sensors that do not impede flow and that are intrinsically separated from the fluid being measured. Examples of these needs include transport of mineral slurries such as powdered coal and powdered lime where particle concentration must be controlled. The consistency of food fluids such as ice cream, coffee and bread dough needs to be monitored and controlled by means of reliable rugged viscosity sensors. Better control of viscoelastic properties of polymer fluids can be achieved by employing suitable sensors. Accordingly, an object of the present invention is to provide an inline blade sensor for a vibratory viscometer that impedes fluid flow to a substantially lesser extent than prior art sensors. Another object of the invention is to provide such a sensor in a configuration that facilitates isolation of the drive and pickup portions of the transducer from the fluid.

Other objects of the invention are to provide transducer-sensor devices that are relatively small, are rugged, easily inserted into industrial process pipes and equipment; that operate over a broad range of viscosities under hot and cold conditions at high pressures; that can be speedily installed and quickly operated in remote and dangerous locations; that are dependable over long stretches of time; that can be easily removed, cleaned and reinstalled; that are capable of providing viscous loss and/or transducer sensor frequency signals for conversion into loss modulus and storage modulus values; that are capable of being vibrated over ranges of frequencies as well as at mechanical resonance; and that are adaptable for use in very viscous and very elastic liquids.

SUMMARY OF THE INVENTION

According to one aspect of the invention there is provided a transducer for a vibratory viscometer. The transducer comprises a support member having an isolation plate. A bar extends through the isolation plate, a peripheral region of the bar being secured and sealed to the adjacent portion of the isolation plate. At least one of the bar and the isolation plate is capable of vibratory movement in a flexure mode. The bar has an upper portion disposed on one side of the isolation plate and a lower portion disposed on the other side of the isolation plate. A sensor plate is secured to the lower portion of the bar. Drive means operatively associated with the upper portion of the bar vibrates the bar with respect to the support member, in a direction parallel to the planes of the major surfaces of the sensor plate. The vibration of the bar is detected by pickup means operatively associated with the upper portion of the bar.

According to another aspect of the invention, there is provided a transducer for a vibratory viscometer, which comprises a support member having an isolation plate. A bar extends through said isolation plate, the compliance of the bar being significantly greater than the compliance of the isolation plate. A peripheral region of the bar is secured and sealed to the adjacent portion of the isolation plate. The bar has an upper portion disposed on one side of the isolation plate and a lower portion disposed on the other side of the isolation plate. A sensor element is secured to the lower portion of the bar. Drive means operatively associated with the upper portion of the bar torsionally vibrates the bar. The torsional vibration of the bar is detected by pickup means operatively associated with the upper portion of the bar.

In the figures identical parts bear identical reference numerals. In FIGS. 2a, 2b, 2c, 2d, 3 and 3a parts which are similar to parts shown in FIGS. 1 and 2 bear identical reference numerals followed by the letter a, b, c, d, e or f respectively.

GENERAL DESCRIPTION

According to one aspect of the invention a transducer oscillates an immersed blade sensor in the direction of the plane of the blade in order to maximize generation of shear waves and to minimize generation of compression waves. The transducer can be used for viscosity measurements with circuitry similar to that disclosed in U.S. Pat. No. 4,488,427; and can be used for viscoelasticity measurements in accordance with circuitry disclosed in U.S. Pat. No. 4,754,640. The transducer of the present invention is also adaptable to microprocessor control.

The transducer includes a rigid bar which is typically of rectangular or circular cross-section. The bar penetrates and is secured and peripherally sealed to a preferably flexible isolation plate which serves to protect the oscillation driver and pickup adjacent one end of the bar from the sensor blade for immersion in a fluid adjacent the other end of the bar.

The isolation plate acts as an intrinsic flexible member of the oscillating system of the transducer, and also constitutes a strong impermeable seal between the fluid and the driver/pickup mechanism.

The isolation plate may be corrugated or ribbed to allow vibratory motion in the desired direction (parallel to the blade major surfaces) while resisting movement in the direction perpendicular thereto.

In another embodiment of the invention the isolation plate is inflexible and the transducer bar is flexible. The bar penetrates the plate but is welded to the plate in the nodal region of the bar, so that vibratory motion induced in the portion of the bar on one side of the isolation plate results in corresponding vibratory motion of the immersed blade sensor on the other side of the isolation plate.

In another embodiment of the invention two small rigid bladelike reflectors are positioned on opposite sides of the oscillating blade—close enough to the oscillating blade to reflect long wavelength shear waves, but far enough from the oscillating blade not to seriously impede the flow of fluid adjacent the oscillating blade. Where the fluid is a suspension or a slurry, the fixed blades are spaced from the oscillating blade a distance sufficient to allow lumps and grains to readily flow by.

In another embodiment of the invention the isolation plate is inflexible and the transducer bar is flexible. The bar penetrates the plate but is welded to the plate in the nodal region of the bar, so that vibratory motion induced in the portion of the bar on one side of the isolation plate results in corresponding vibratory motion of the immersed blade sensor on the other side of the isolation plate. The bar is vibrated in a torsional mode. One end of the bar may have a driver/pickup arrangement similar to that disclosed in U.S. Pat. No. 4,488,427. The other end of the bar may have a spherical or other sensor tip immersed directly in the fluid to be measured or it may have an arm to which a blade is attached, with the major surfaces of the blade being perpendicular to the longitudinal axis of the bar. In the latter case the vibratory motion of the immersed blade is in the plane of its major surfaces and is more or less circumferential, depending on the length of the arm.

In the various embodiments of the invention, measuring apparatus coupled to the driver/pickup circuitry is capable of measuring viscous loss or viscosity-density product from the power required to maintain oscillation of the blade at a constant amplitude; and in the case of viscoelastic fluids the apparatus is capable of converting resonance frequency changes into the elastic component of viscous loss. The apparatus can also use frequency change information to determine the fluid density. Such measuring apparatus is known in the art and does not constitute any part of the present invention.

DETAILED DESCRIPTION

Figure 1:
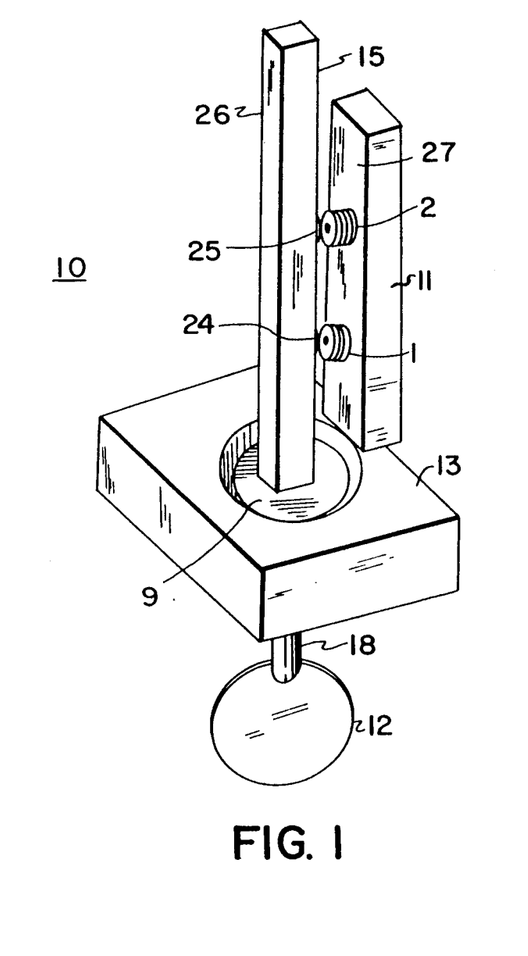
FIG. 1 is an isometric drawing showing a transducer utilizing a blade sensor and having a flexible isolation plate, according to a first embodiment of the present invention.
Figure 2:
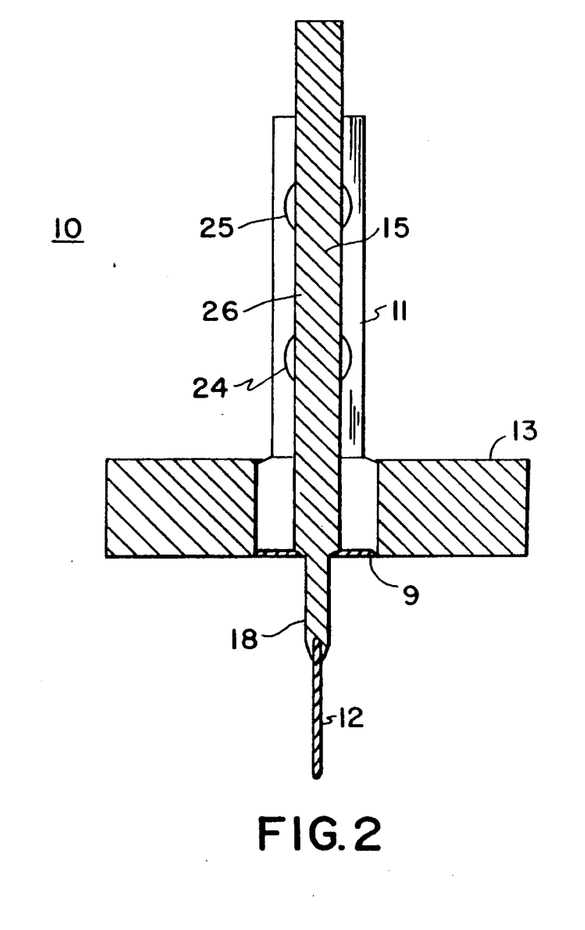
FIG. 2 is a front cross-sectional elevation view of the transducer shown in FIG. 1.

First Embodiment—FIGS. 1 and 2

The first embodiment of the transducer 10 shown in FIGS. 1 and 2 consists of an L-shaped support member having a base part 13 and a driver/pickup supporting part 11. The support member is preferably solid and made of a type 316 stainless steel. The base part 13 is adapted to be mounted in an opening of a pipe, vessel or other enclosure containing a fluid the viscosity or related parameters of which are to be measured.

The base part 13 of the support member has a portion 9 of reduced thickness which serves as an isolation plate for isolating the portion of the transducer 10 which is disposed outside the pipe, vessel or other enclosure containing the fluid being measured, from exposure to the fluid or its vapors; in order to (i) maintain the pressure or vacuum to which the fluid is subjected, (ii) seal the pipe, vessel or other enclosure from the atmosphere, and (iii) prevent damage to the portions of the transducer outside the pipe, vessel or other enclosure which might otherwise result from contact with the fluid or its vapors.

A unitary vibratory bar 15 extends through and is secured and peripherally sealed to the isolation plate 9. The bar 15 is relatively rigid as compared to the isolation plate 9, which is sufficiently compliant so as to have only a small effect on the amplitude and frequency of vibration of the bar 15.

The bar 15 has an upper portion 26 disposed in juxtaposition with the driver/pickup supporting part 11 of the support member, and an immersible lower portion 18; the bar portions 18 and 26 being isolated from each other by the isolation plate 9. The bar 15 is preferably solid and made of a type 316 stainless steel; and the periphery of the bar is welded or silver brazed to the adjacent portion of the isolation plate 9.

The upper portion 26 of the bar 15 has a rectangular cross-section to facilitate interaction with the driver and pickup elements of the transducer, while the lower portion 18 thereof has a circular cross-section to reduce the turbulence produced by flow of the fluid to be measured past the lower portion 18.

A driver magnetic pole piece 24 made of Invar is secured to the upper portion 26 of the vibratory bar 15. A pickup magnetic pole piece 25 made of Invar is secured to the upper portion 26 of the vibratory bar 15 at a position preferably further away from the isolation plate 9 than is the driver pole piece 24.

An electromagnetic driver coil 1 is mounted on the driver/pickup supporting part 11 of the support member at a position adjacent the driver pole piece 24. An electromagnetic pickup coil 2 is mounted on the driver/pickup supporting part 11 of the support member at a position adjacent the pickup pole piece 25.

An immersible sensor 12 in the form of a narrow blade-like disk or plate, is secured to the end of the lower (circular) portion 18 of the bar 15.

The disk 12 is oriented with its major surfaces in a plane perpendicular to the surface 27 of the driver/pickup supporting part 11 of the support member upon which the driver coil 1 and pickup coil 2 are mounted. Thus when the driver coil 1 is actuated by an AC signal to cause the upper portion 26 of the vibratory bar 15 to vibrate toward and away from the supporting part 11, the lower portion 18 of the bar 15 vibrates away from and toward the supporting part 11, causing the disk 12 to vibrate in the plane of its major surfaces.

The transducer 10 is installed so that the base part 13 of the support member is disposed and sealed in an opening in a pipe, vessel or other fluid container, with the disk 12 immersed in the fluid therein. The base part 13 is positioned so that the disk 12 is oriented so that its major surfaces are parallel to the direction of flow of the fluid being measured, i.e. so that disruption of flow due to the presence of the disk is minimized.

The transducer shown in FIGS. 1 and 2, as well as all the other embodiments of the present invention, may be vibrated at its mechanical resonant frequency by signals applied to the driver coil 1 by a feedback circuit of the type disclosed in U.S. Pat. No. 4,488,427. The input to the feedback circuit is provided by the output of the pickup or detector coil 2; and the output of the feedback circuit is connected to the driver coil 1. The AC signal applied to the driver coil 1 by the feedback circuit causes a varying magnetic field to be applied by the driver coil 1 to the pole piece 24 to cause the relatively rigid bar 15 to flexurally oscillate at the mechanical resonant frequency of the bar-isolation plate-fluid system.

The bar 15 vibrates, oscillates or rocks through an extremely small angle (typically less than 0.001°), slightly bending the compliant plate 9 as the bar vibrates. The plate 9 is made sufficiently thin to allow it to flex in response to the rocking of the bar 15. If the bar 15 is provided with an elongated rectangular rather than square cross-section, it is oriented such that the pole pieces 24, 25 are attached to the more narrow side of said cross-section. This provides a more rigid vibratory element since the rocking occurs about the wider part of the rectangular bar 15. The oscillations due to the rocking motion of the bar 15 are detected by means of pole piece 25 and detector coil 2.

The resonance characteristic of the transducer exhibits a high quality factor ("Q"), on the order of $4.3 \times 10^3$, with low internal loss ("$Q^{-1}$"); so that the transducer has a sharp resonance peak, which is often advantageous in this type of a transducer.

Figure 2A:
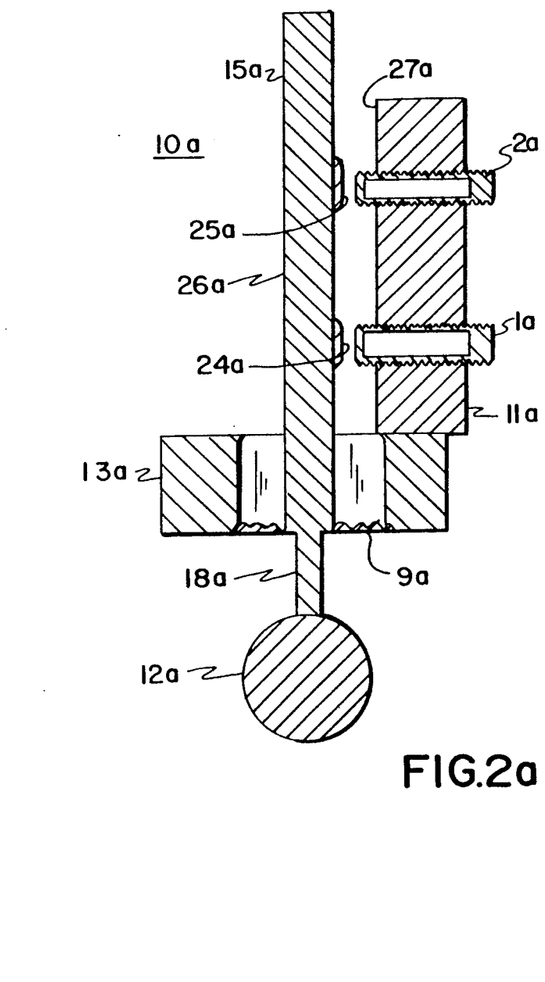
FIG. 2a is a side cross-sectional elevation view showing a transducer according to a second embodiment of the invention, having a corrugated isolation plate.

Second Embodiment—FIG. 2a

In order to provide accurate viscosity information with minimal error due to the generation of compression waves as opposed to the desired shear waves in the fluid, any vibration of the disk 12 in a direction other than the plane of the disk should be minimized. For this purpose the embodiment shown in FIG. 2a (which is in all other respects the same as that shown in FIGS. 1 and 2) has an isolation plate 9a with a corrugated or ribbed configuration. This structure allows the isolation plate to flex much more easily in the desired direction parallel to the major surfaces of the disk 12, while preventing flexure in the direction perpendicular to the desired direction.

Figure 2B:
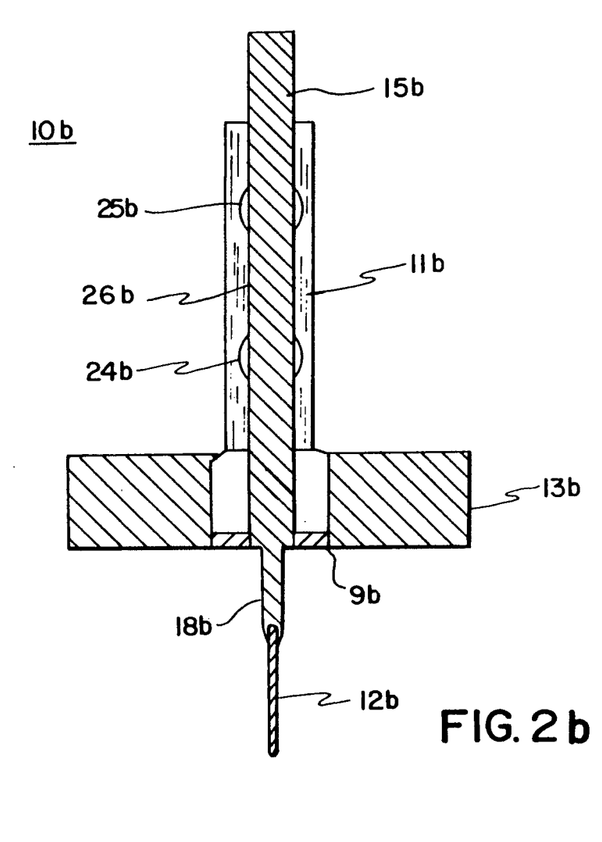
FIG. 2b is a front cross-sectional elevation view showing a transducer according to a third embodiment of the invention, having a rigid isolation plate.

Third Embodiment—FIG. 2b

The third embodiment of the invention as shown in FIG. 2b (which is in all other respects the same as that shown in FIGS. 1 and 2), has an isolation plate 9b which is thicker than the isolation plate 9 and is relatively rigid as compared to the isolation plate 9.

The isolation plate 9b is also relatively rigid as compared with the vibratory bar 15b. If the bar 15 is provided with an elongated rectangular rather than square cross-section, it is oriented such that the pole pieces 24, 25 are attached to the wider side of said cross-section. This provides a more compliant vibratory element since the rocking occurs about the narrower part of the rectangular bar 15.

Whereas the first embodiment allows for practically no bending of the bar, the third embodiment produces a greater amount of bending. The bar 15b bends at its natural resonance frequency in a mode similar to the free-free beam mode described in a book by Don Hartog entitled "Mechanical Vibrations", page 432, McGraw-Hill Book Co., 1956. The exception to the Hartog model is that the bar 15b is welded to the isolation plate 9b at a nodal region of the bar.

Figure 2C:
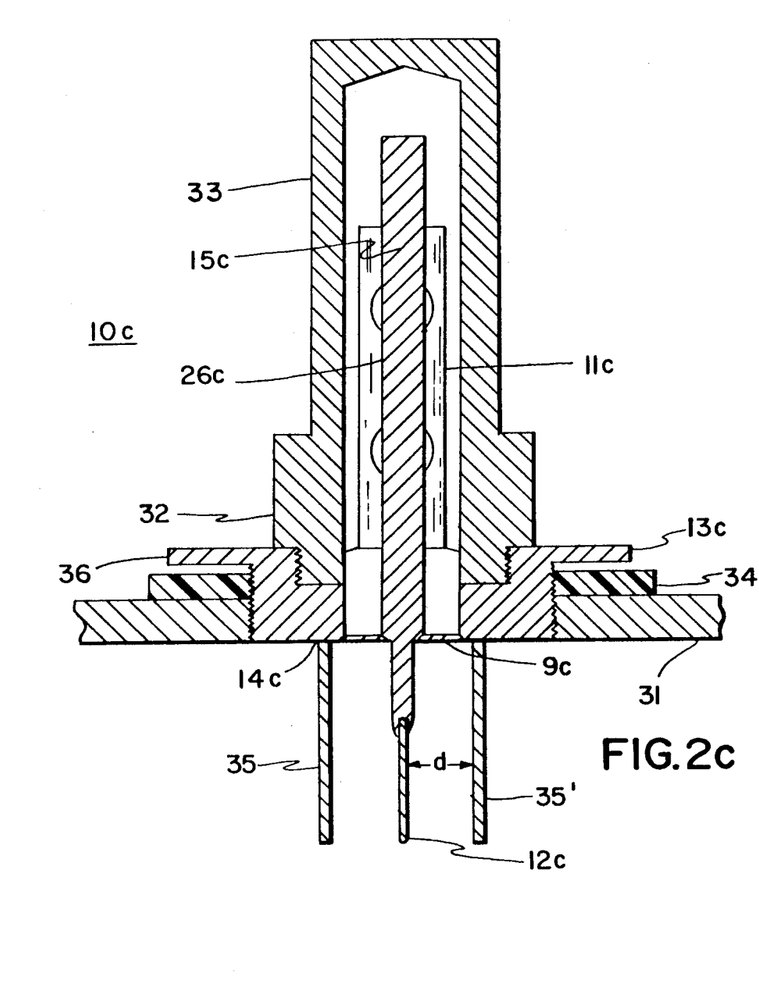
FIG. 2c is a front cross-sectional elevation view of a transducer according to a fourth embodiment of the invention, having reflecting blades positioned to reflect long wavelength waves in order that the viscoelastic properties of highly viscous liquids possessing elasticity can be determined more accurately.

Fourth Embodiment—FIG. 2c

In the embodiment shown in FIG. 2c (which is otherwise substantially the same as that shown in FIGS. 1 and 2), rigid reflector blades 35 and 35' are disposed on opposite sides of, parallel to and near each face of the sensor blade 12c.

The reflector blades 35 and 35' provide a more accurate measurement of the viscoelastic properties of liquids. They are attached to the underside of the base part 13c of the support member at region 14c thereof.

In viscoelastic fluids the propagation of shear waves generated by the vibrating sensor may affect rheological measurements. To provide more accurate readings parallel reflector plates are positioned on opposite sides of the sensor element 12c in order to reflect shear waves having long wavelengths.

The distance "d" between each reflector and the adjacent sensor face is dependent upon the viscoelasticity of the fluid being measured. Preferably, the distance d (FIG. 2c) between the sensor and the reflecting plates is about one-fortieth (1/40) of the wavelength of the shear waves. To know the wavelength, one must know the complex (i.e. real and quadrature components of the) viscosity of the material tested, since the wavelength is directly related to the viscoelastic properties of the material. See J. S. Schrag, "Deviation of Velocity Gradient Profiles from the "Gap Loading" and Surface Loading Limits", Transactions of the Soc. Rheology, 21:3, 399–413 (1977).

As is also shown in FIG. 2c, the isolation plate 9c is an integral part of the base part 13c of the support member, which is mounted into the wall of the pipe, vessel, container or equipment 31. The walls of the pipe, vessel, container or equipment 31 may substitute for reflector plates. A nut 34 is used to secure the base part 13c of the transducer 10c to the wall 36. An indicator marking (not shown) on the outer surface of transducer cap 33 visible to the installer allows the transducer to be positioned in such a manner that the sensor blade 12c is parallel to the direction of fluid flow.

The cap 33 is fastened to the top of the base part 13c of the support member via a threaded connection 32. The cap 33 houses the electrical leads to the driving and pickup or detector coils.

Figure 2D:
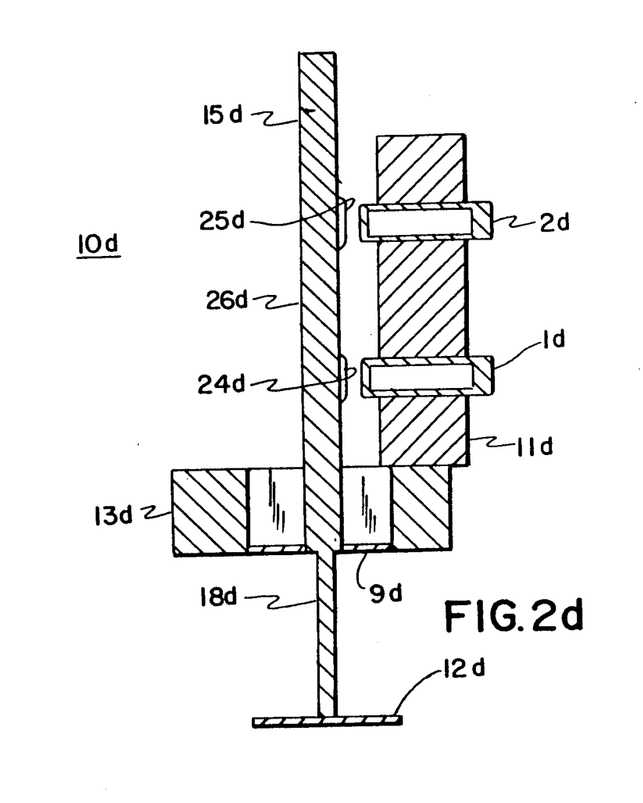
FIG. 2d is a side cross-sectional elevation view of a transducer according to a fifth embodiment of the invention, having a flexural mode vibratory plate sensor.

Fifth Embodiment—FIG. 2d

The fifth embodiment of the invention, viz. the transducer 10d shown in FIG. 2d, vibrates bar 15d in a similar manner to the embodiment of FIGS. 1 and 2; except that in the FIG. 2d embodiment sensor 12d has its major surfaces oriented perpendicular to the longitudinal axis of the lower portion 18d of the bar 15d. This orientation of the sensor 12d provides for minimal disruption of flow lines generated by continuously moving material through pipelines or the like.

Figure 3:
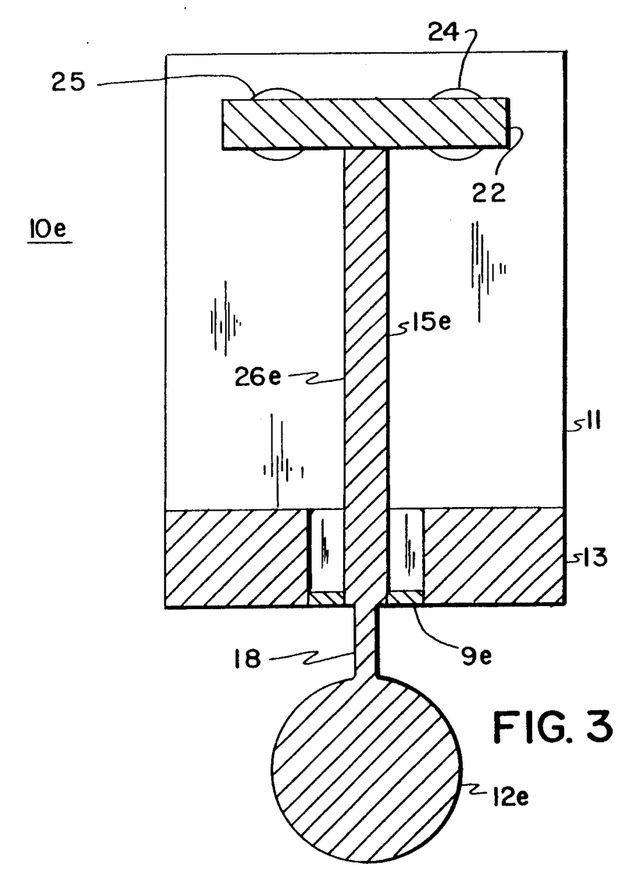
FIG. 3 is a front cross-sectional view of a transducer having a torsional mode vibratory spherical sensor according to a sixth embodiment of the invention.

Sixth Embodiment—FIG. 3

The sixth embodiment of the invention, viz. the transducer 10e shown in FIG. 3, vibrates the bar 15 in a torsional mode. For this purpose a cross arm 22 is secured to the upper end of the bar, the pole pieces 24, 25 being mounted on the cross arm adjacent opposite ends thereof.

The electromagnetic drive and pickup coils 1, 2 (not visible in FIG. 3) are mounted on the drive/pickup supporting part 11 of the support member, at positions adjacent to the pole pieces 24, 25 respectively.

This cross arm arrangement for providing torsional vibration of the bar is similar to that shown in FIGS. 1 and 2 of U.S. Pat. No. 4,488,427. However, the transducer of U.S. Pat. No. 4,488,427 utilizes a compliant hollow cylindrical sheath surrounding a relatively rigid bar, the sheath being oscillated in a torsional mode in response to vibratory angular movement of the bar. On the other hand, in the embodiment of the present invention shown in FIG. 3, the relatively compliant bar 15 is secured and peripherally sealed to a relatively rigid isolation plate 9e which to provide a vibrational node at the junction of the bar and isolation plate.

The motion of the bar 15 results in a twisting of the bar as opposed to the (i) flexing of the isolation plate according to the first, second and fourth embodiments of the invention (FIGS. 1, 2a, 2c respectively) and the (ii) flexing of the bar according to the third embodiment of the invention. The same thickness of the isolation plate 9b as is shown in the third embodiment (FIG. 2b) may be used to provide a rigid isolation plate. The bar 15 is welded or silver brazed to the isolation plate in its nodal region where the bar pierces the isolation plate 9e.

The sensor 12e secured to the end of the lower (circular) portion of the bar 18 has a spherical shape; although a cylindrical sensor may also be used.

When the upper portion 26e of bar 15 is twisted by the interaction of the drive coil with the pole piece 24, a corresponding twist occurs in the lower section 18 of the bar.

Figure 3A:
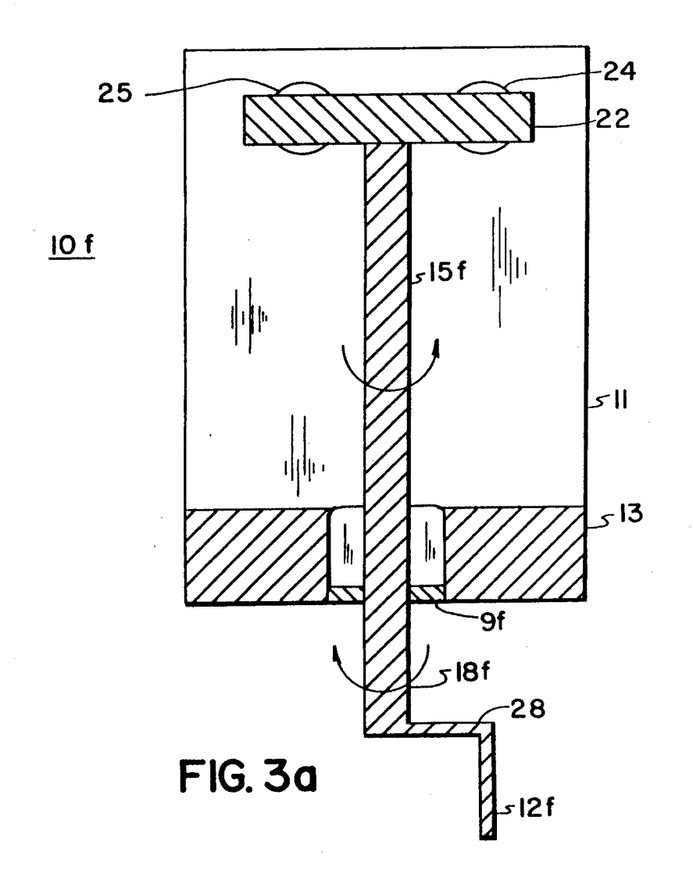
FIG. 3a is a front cross-sectional view of a transducer having a torsional mode vibratory sensor according to a seventh embodiment of the invention, in the form of a plate mounted on an arm so that torsional vibration of a vibratory bar of the transducer results in generally circumferential vibration of the plate in the plane of its major surfaces.

Seventh Embodiment—FIG. 3a

The seventh embodiment of the invention, viz. the transducer 10f shown in FIG. 3a, is similar to the sixth embodiment, except that the lower portion 18f of the bar 15f has a larger diameter and a right angle bend forming an arm 28, a disc-shaped sensor 12f being secured to the end of the arm.

With this arrangement the major surfaces of the sensor 12f are oriented in planes parallel to the longitudinal axis of the bar 15f. As a result the vibratory motion of the immersed sensor is in the plane of its major surfaces and is generally circumferential, the length of the arm 28 determining the angular amplitude of vibration of the sensor with respect to the longitudinal axis of the arm.

Experimental Tests

Transducers of the types shown in the drawings were constructed and tested. During these tests the area of the major surfaces of the sensor and the thickness of the isolation plate were varied.

The flexural vibration of the transducers tested was found to be satisfactory for the purpose of measuring viscous properties of fluids. With these transducers the percent amplitude of oscillation (as compared to the amplitude of oscillation in air), resonance frequency, $Q^{-1}$ for the transducer and fluid system, and the power required to maintain oscillation at a given amplitude were determined to be related to and be measures of (i) fluid viscosity-density product and (ii) the extent of the elastic character of a viscoelastic liquid.

Recordings were made by means of the Nametre Viscoelasticity Rheometer manufactured by Nametre Company, 101 Forrest Street, Metuchen, N.J. 08840.

Amplitude Analysis

The correlation between the percent amplitude and frequency of mechanical resonance peaks of the transducer and the viscosity-density product of the fluids tested was determined by means of a transducer 10b like that shown in FIG. 2b, having a circular blade 0.050 cm thick with a total major surface area of 11.4 cm². The flexible bar 15b had a length of 18.3 cm. The bar was of rectangular cross-section throughout, with a cross-sectional width of 0.95 cm. and cross-sectional depth of 0.95 cm. The isolation plate 9b was 0.159 cm. in thickness. The test results were as shown in Table I.

TABLE I

| Viscosity-Density | % Amplitude | Resonant Freq. |
|---|---|---|
| Air (negligible cP) | 100% | 195.4 Hz. |
| 26 cP | 91 | 195.4 |
| 5000 | 41 | 194.9 |
| 66400 | 21 | 194.7 |
| 500000 | 15 | 194.5 |

From a plot of log viscosity-density product vs. percent amplitude of oscillation, the viscosity-density product of an unknown fluid sample is easily determined.

For example, a liquid showing 30% amplitude of transducer vibration would have a viscosity-density product VD of 18,000 mPa.s.g/cm³. In the instrument referred to above, the equation $VD = \text{Log}^{-1}([195.71 + f_r]/0.214)$ was found applicable to variations of viscosity-density product VD with resonance frequency $f_r$. Thus the frequency of 194.8 Hertz obtained when the blade was immersed means the viscosity of the sample was 18,000 mPa.s.

Internal Friction Analysis $Q^{-1}$ designates the loss or internal friction of an oscillating mechanical system. $Q^{-1}$ can be determined from the relation $$Q^{-1} = (f_3 - f_1)/\sqrt{3}\, f_r,$$

where $f_1$ and $f_3$ are half peak frequency values (i.e. the frequencies above and below the resonance frequency at which the amplitude is 50%) and $f_r$ is the peak resonance frequency. Viscosity (assuming a density of 1) and internal friction $Q^{-1}$ are tabulated in Table II. For this test the flexible bar 15b had a length of 16.3 cm. The bar was of rectangular cross-section throughout, with a cross-sectional width of 0.61 cm. and cross-sectional depth of 0.99 cm. The isolation plate 9b was 0.079 cm. in thickness.

TABLE II

| Viscosity (Density = 1) of Sample | $Q^{-1}$ Instrument + Sample | $Q^{-1}$ Sample |
|---|---|---|
| Air | $5.6 \times 10^{-4}$ | $0 \times 10^{-4}$ |
| 0.98 mPa·s | $9.3 \times 10^{-4}$ | $3.7 \times 10^{-4}$ |
| 7.63 | $15.9 \times 10^{-4}$ | $10.3 \times 10^{-4}$ |
| 26.0 | $23.4 \times 10^{-4}$ | $17.8 \times 10^{-4}$ |

The viscosity-density products of the samples in Table II were found to be proportional to the internal friction $Q^{-1}$ squared. The relation $VD = 8.333 \times 10^6 (Q^{-1})^2 - 0.5913$ was found to apply. Thus, for example, a liquid having a $Q^{-1}$ of $14 \times 10^{-4}$ would have a viscosity of 15.6 mPa.s.

A significant reduction in the resonance frequency to 49.7 Hertz was obtained by reducing the thickness of the isolation plate to 0.0305 cm. In this case the bar was relatively rigid with respect to the isolation plate, which was relatively compliant. The power P (in watts) required to maintain a constant amplitude of oscillation is tabulated in Table III for several viscosities.

TABLE III

| Viscosity-Density | Total Power | Viscous Power |
|---|---|---|
| 0.98 mPa·s × D | $1.13 \times 10^{-3}$ watts | $0 \times 10^{-3}$ watts |
| 8630 | $8.01 \times 10^{-3}$ watts | $6.88 \times 10^{-3}$ watts |
| 30200 | $17.3 \times 10^{-3}$ watts | $16.2 \times 10^{-3}$ watts |

Thus, for example, a sample requiring a power of $10^{-2}$ watts to maintain a constant amplitude has a viscosity-density product of 10,000 mPa.s × D (where D is the density of the sample) as determined by interpolating the data in Table III.

A viscoelastic polymer additive was measured by means of a transducer of the type shown in FIGS. 1 and 2. A frequency drop of only 0.1 Hz was obtained as compared to the 0.2 Hz. decrease obtained with a purely viscous liquid of similar viscosity. This test proves that the transducer can be used to measure viscoelastic properties of liquids.

Sensor Blade Area

Increasing the area of the sensor blade 9 resulted in a substantial decrease in the resonance frequency. This large frequency shift enables elasticity measurements of viscoelastic liquids with acceptable accuracy. The data in Table IV were obtained with a transducer tested with blades with three different areas; first in air, and then with the blade immersed in a liquid having a viscosity of 1260 mPa.s.

TABLE IV

| Blade Area | Resonance Freq. In Air | Resonance Freq. In Liquid |
|---|---|---|
| 10.7 cm.² | 195.6 Hz. | 195.5 Hz. |
| 20.6 | 194.4 | 193.9 |
| 58.0 | 244.9 | 194.9 |

Isolation Plate Thickness and Composition

Changes in the thickness and composition of the isolation plate result in the corresponding changes in resonance frequencies (for a mode wherein the isolation plate is relatively rigid and the bar is relatively flexible, and/or a mode wherein the bar is relatively rigid and the isolation plate is relatively flexible) shown in Table V.

TABLE V

| Plate Thickness (cm.) | Resonance Freqs. In Air | Mode Plate/Bar |
|---|---|---|
| 0.079 (Brass) | 71.1 Hz, 618.4 Hz | flex./rigid |
| 0.159 (316 stainless steel) | 195.3 Hz, 1587.80 Hz | rigid/flex. |
| 0.031 (316 stainless steel) | 49.65 Hz, — | flex./rigid |

The stiffness of the bar 15 increases as its thickness increases. Likewise, the stiffness of the isolation plate increases as its thickness increases. Therefore a transducer that oscillates by flexure of the isolation plate may also oscillate when the plate is made rigid and the thickness of the bar is reduced.

Other methods may be used to process the output of the pickup coil of the transducer according to the present invention to obtain measurements of the viscous properties of the fluid in which the sensor is immersed. For example, variations in the phase of the (AC) signal generated by the pickup coil relative to that of the signal applied to the drive coil may be used for this purpose.

The internal workings of the transducer are separated from the fluid by an isolation plate which may be rigid or compliant. Test data show that measurements of viscous properties of fluids over a wide viscosity range are possible with the transducer of the present invention.

We claim:

1. A transducer for a vibratory viscometer, comprising:
    a support member having an isolation plate;
    a bar extending through said isolation plate, the compliance of said bar being significantly greater than the compliance of said isolation plate, a peripheral torsion nodal region of said bar being secured and sealed to the adjacent portion of said isolation plate, said bar having an upper portion disposed on one side of said isolation plate and a lower portion disposed on the other side of said isolation plate;
    a sensor element secured to the lower portion of said bar;
    drive means operatively associated with the upper portion of said bar for torsionally vibrating said bar; and
    pickup means operatively associated with the upper portion of said bar for detecting the torsional vibration of said bar.

2. A transducer for a vibratory viscometer, comprising:
    a support member having a base part and a driver/pickup supporting part, said base part containing a rigid isolation plate;
    an elongated bar extending through said isolation plate, a peripheral region of said bar being secured and sealed to the adjacent portion of said isolation plate, said bar having an upper portion disposed on one side of said isolation plate and a lower portion disposed on the other side of said isolation plate, at least a part of said lower portion having a longitudinal axis;
    a sensor element secured to the lower portion of said bar;
    drive means operatively associated with the upper portion of said bar for vibrating said bar with respect to the base part of said support member, to impart a reciprocating motion to the lower portion of said bar; and
    pickup means operatively associated with the upper portion of said bar for detecting the vibration of said bar.

3. A transducer for a vibratory viscometer, comprising:
    a support member having a base part and a driver/pickup supporting part having a transducer mounting surface including drive means and pickup means, said base part containing a relatively rigid isolation plate, and wherein said drive means and pickup means are located in said driver/pickup supporting part exclusively;
    an elongated relatively compliant unitary bar extending through said isolation plate, a peripheral region of said bar being secured and sealed to the adjacent portion of said isolation plate, said bar having an upper portion of rectangular cross-section to facilitate interaction with said drive means and pickup means disposed on one side of said isolation plate and a lower portion disposed on the other side of said isolation plate;

a sensor tip in the form of a narrow blade-like disk or plate having opposed major surfaces secured to the lower portion of said bar and adapted for immersion in a fluid;

drive means operatively associated with the upper portion of said bar for flexurally oscillating said bar with respect to the base part of said support member at the mechanical resonant frequency of the bar-isolation plate-fluid system, in a direction parallel to the planes of the major surfaces of said sensor tip and perpendicular to the transducer mounting surface of said driver/pickup supporting part, so as to maximize generation of shear waves and minimize generation of compression waves in said fluid; and pickup means operatively associated with the upper portion of said bar for detecting the oscillation of said bar.

4. The transducer according to claim 3, wherein the upper portion of said bar has a non-square rectangular cross-section with the narrower sides of said upper portion parallel to the major surfaces of said sensor plate.

5. A transducer for a vibratory viscometer, comprising:

a support member having a base part and a driver/pickup supporting part, said base part containing an isolation plate;

an elongated bar extending through said isolation plate, the compliance of said bar being substantially different from the compliance of said isolation plate, a peripheral region of said bar being secured and sealed to the adjacent portion of said isolation plate, said bar having an upper portion disposed on one side of said isolation plate and a lower portion disposed on the other side of said isolation plate;

a sensor element secured to the lower portion of said bar, said sensor element comprising a plate having major surfaces parallel to the longitudinal axis of the upper portion of said bar;

drive means operatively associated with the upper portion of said bar for torsionally vibrating said bar about the longitudinal axis thereof to vibrate said plate in a direction generally circumferential with respect to said longitudinal axis and parallel to the major surfaces of the plate; and pickup means operatively associated with the upper portion of said bar for detecting the torsional vibration of said bar.

6. A transducer for a vibratory viscometer, comprising:

a support member having a base part and a driver/pickup supporting part, said base part containing an isolation plate;

an elongated bar extending through said isolation plate, a peripheral region of said bar being secured and sealed to the adjacent portion of said isolation plate, said bar having an upper portion disposed on one side of said isolation plate and a lower portion disposed on the other side of said isolation plate, at least a part of said lower portion having a longitudinal axis;

a sensor element secured to the lower portion of said bar, said sensor element comprising a plate secured to an end of said lower portion of said bar in such a manner that the major surfaces of said plate are oriented perpendicular to said longitudinal axis;

drive means operatively associated with the upper portion of said bar for vibrating said bar with respect to the base part of said support member, to impart a reciprocating motion to the lower portion of said bar; and pickup means operatively associated with the upper portion of said bar for detecting the vibration of said bar.

7. The transducer according to claim 6, wherein the compliance of said bar is substantially greater than the compliance of said isolation plate.

* * * * *